United States Patent

Cribbs et al.

Patent Number: 6,071,239
Date of Patent: Jun. 6, 2000

[54] METHOD AND APPARATUS FOR LIPOLYTIC THERAPY USING ULTRASOUND ENERGY

[76] Inventors: Robert W. Cribbs, 4001 Lakeview Dr., Placerville, Calif. 95667; Carl W. Hennige, 108 S. Grant La., Folsom, Calif. 95630

[21] Appl. No.: 08/991,631

[22] Filed: Oct. 27, 1997

[51] Int. Cl.⁷ ................................................ A61B 8/00
[52] U.S. Cl. .................................. 600/439; 601/3
[58] Field of Search .................................. 600/439, 437, 600/443, 447, 2, 10, 407; 601/2, 3

[56] References Cited

U.S. PATENT DOCUMENTS

| 3,941,122 | 3/1976 | Jones. |
| 3,958,559 | 5/1976 | Glenn et al. |
| 4,757,820 | 7/1988 | Itoh. |
| 4,875,487 | 10/1989 | Seppi. |
| 4,938,216 | 7/1990 | Lele. |
| 5,143,063 | 9/1992 | Fellner ............................................. 601/3 |
| 5,419,761 | 5/1995 | Narayanan et al. |

OTHER PUBLICATIONS

1987, J.B.Lippincott Company Philadelphia (Publisher) "Principles and Practice of Radiation Oncology", Authors: C.A. Perez, M.D., L.W. Brady, M.D.; Chapter 15 "Hyperthermia", pp. 329–331.

*Primary Examiner*—Marvin M. Lateef
*Assistant Examiner*—Ali M. Imam
*Attorney, Agent, or Firm*—Harry G. Weissenberger, Esq.

[57] ABSTRACT

Fat cells in a living patient are noninvasively destroyed without separating the skin from the body by applying to the fat layer high intensity focused ultrasound simultaneously in a multiplicity of discrete focal zones produced by a single transducer array. A novel phasing apparatus for producing a widely variable set of focal zone patterns for lipolytic therapy and other purposes is disclosed.

7 Claims, 6 Drawing Sheets

- ● = focus 1
- ☐ = focus 2
- ■ = focus 3
- ○ = focus 4

FIG. 10

METHOD AND APPARATUS FOR LIPOLYTIC THERAPY USING ULTRASOUND ENERGY

FIELD OF THE INVENTION

This invention relates to a method of ablating human fat by ultrasonically destroying cells in a selectable pattern particularly suited to lipolytic therapy, and to an apparatus for producing that pattern.

BACKGROUND OF THE INVENTION

The permanent removal of fat from the human body is a highly desirable but very difficult undertaking. Dieting or learning good eating habits are effective to a degree but are not long-range solutions for most people; nor are these approaches effective in situations where undesirable fatty deposits are localized in the body.

Typically, fat cells are produced by the human body only until puberty. Thereafter, the then existing fat cells expand and contract with the accumulation and release of fat but do not change in number. If fat cells are destroyed after puberty, the remaining fat cells will attempt to compensate to some degree, but about 70% of the fat in the destroyed cells is never recovered by the body.

A conventional method of destroying fat cells is lipolytic therapy, or liposuction, in which all or part of the subcutaneous fat cell layer in the target areas of the body is surgically removed. This is a highly invasive and potentially disfiguring procedure with a prolonged and uncomfortable recovery due to the resulting separation of the skin from the body. For that reason, liposuction is not practical for weight control therapy, but only for body reshaping in limited areas.

In order to make fat cell destruction therapy practical for weight control, it is necessary to so destroy fat cells that a sufficient network of subcutaneous tissue remains to support the skin while the destroyed fat cells are absorbed and the subcutaneous tissues heal. In other words, fat cells must be destroyed in small, discrete, unconnected areas in any given treatment. At the same time, it is necessary to destroy fat cells in sufficient number and rapidly enough to make such therapy practical. No prior art has been able to accomplish this.

Also, there have been attempts in the prior art to selectively destroy tissue by hyperthermia, i.e. ultrasonic heating. In the prior art, however, such procedures have raised temperatures in the destruction zone to about 40° C. At that temperature, it takes minutes or even hours of exposure to destroy tissue.

SUMMARY OF THE INVENTION

The present invention makes lipolytic therapy practical for weight control as well as for body reshaping by using high intensity, sharply focused ultrasound (HIFU) to selectively destroy fat cells at discrete subcutaneous points in a pattern which achieves substantial fat cell removal by ablation in a reasonable time without incisions and without separating any substantial skin areas from the body, so as to allow natural absorption of the destroyed fat cells and healing of the subcutaneous layers.

For this purpose, the invention uses a novel ultrasonic array that transmits a high intensity beam focused in multiple discrete subcutaneous areas by an inventive phasing arrangement of the elements of the transducer array.

BRIEF DESCRIPTION OF THE DRAWINGS

FIG. 5b is a section along line 5b—5b of FIG. 5a;

DESCRIPTION OF THE PREFERRED EMBODIMENT

High intensity focused ultrasound (HIFU) has been used successfully in the prior art to destroy tissue, particularly in prostate surgery. The HIFU beam concentrates enough heat energy in its focal zone to kill cells lying in that zone, but it does not significantly damage cells outside its focal zone. It is therefore possible with HIFU to destroy a highly localized group of cells from an externally accessible nearby site without cutting or damaging the tissue surrounding the cell group (e.g., killing prostate tissue along the urethra from the rectum).

The application of HIFU technology to the selective and substantially instantaneous (i.e. ablative) destruction of subcutaneous fat cells from outside of the body does, however, present significant problems. A fundamental problem is the fact that when a transducer array is applied to the skin for the transcutaneous transmission of ultrasound energy, the body's fat layer has a much smaller dimension in the direction axial to the ultrasound beam than in the directions transverse to it. The focal zone of the beam, however, is relatively long in the axial direction and narrow in the transverse directions.

The axial dimension of the focal zone can be shortened, if it is longer than the depth of the fat cell layer, by increasing the frequency of the ultrasonic signal. However, because the ratio between length and width of the focal zone remains constant, the focal zone volume becomes very small, and the destruction of a few pounds of fat tissue would take many hours.

One might consider increasing the power and either physically scanning the transducer faster, or using an array and electronically scanning the beam faster. Neither is satisfactory because, at a certain beam intensity, cavitation occurs, and further increases in intensity do not produce a proportional increase in the rate of heating. Furthermore, bubbles produced by cavitation cause the beam to behave in an unpredictable way.

The present invention makes ultrasonic fat cell destruction practical even in patients with a relatively thin fat cell layer, by using an array to create multiple focal zones at the same time. The transducer power is used to bring each zone up to an ablative level (i.e. ca. 80° C.) just below or at cavitation rather than to put one zone well beyond cavitation. These zones can be laterally arranged or arranged in an arbitrary matrix. This approach avoids the cavitation problem, and also has other advantages:

1) The axial dimension can be kept small or adjusted as necessary by electronically controlling the dimensions of the focal zones.

2) The rate of cell destruction can be high because the sum of the volumes of the multiple zones is high.

3) The focal zone matrix can be adjusted to different shapes and tapers during treatment to accommodate different individuals.

4) The focal zones can be adjusted to allow a sponge-like matrix of live tissue to remain between the destroyed tissue. This is a big advantage over liposuction where the entire layer is destroyed, essentially disconnecting the skin from the body. With liposuction, the patient must be put in a body suit to hold the skin to the body during recovery. By preserving the live matrix, the patient may leave treatment and return to normal activity with minimal or no recovery time.

The technology of this invention is not limited to the destruction of fat cells. It can equally well be used for other medical conditions involving subcutaneous cells that require elimination. They include enlarged male breasts, benign fatty tumors, lipomatosis, excessive sweating under arms, post traumatic adipose tissue, and others.

In other informal organs, broad lateral coverage and narrow axial coverage may not be needed, but often shaping the destruction zone is useful and sometimes necessary. In these cases, the multiple beam will be more satisfactory than moving the beam because it allows higher frequencies to be used which provide smaller focal spots and therefore more precise boundaries of the region of destroyed tissue.

Figure 1:
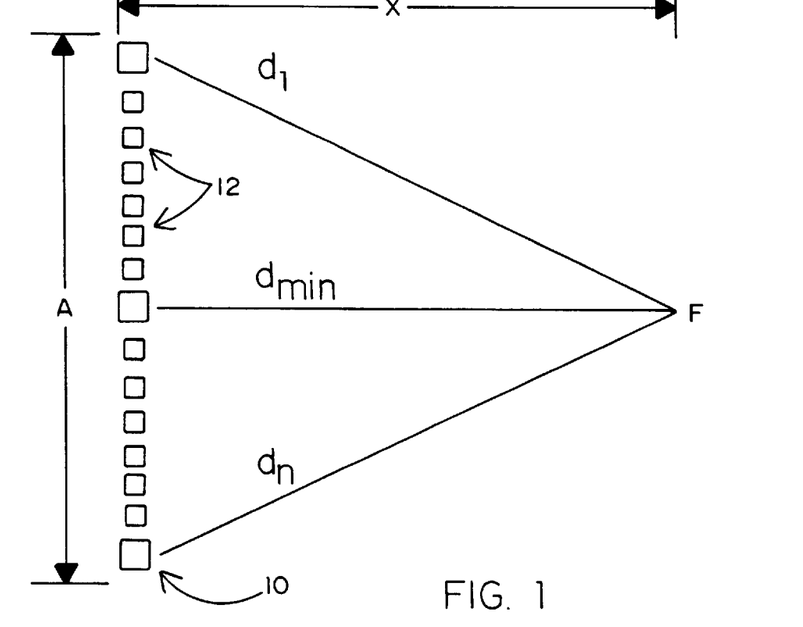
FIG. 1 is a schematic diagram illustrating the focusing of a phased transducer array.

The inventive apparatus which produces multiple focal zones for the above-described purposes is a flat or curved planar transducer array with a novel phasing arrangement. FIG. 1 schematically shows a linear array 10 of individual transducers 12. By exciting each of the transducers 12 with a different phase of the ultrasound signal, the array 10 can produce an ultrasonic beam focused at any desired location in its field of view.

In order to focus the beam of array 10 at a focal spot F, the respective phase applied to any given transducer element 12 of the array 10 is $$\phi_{e,f} = \left(\frac{d_e - d_{min}}{\lambda}\right) \times 360°, \text{ modulo } 360 \quad (1)$$

in which $\phi_{e,f}$ is the phase for the $e^{th}$ element for the $f^{th}$ focal spot, $d_e$ is the distance from the given array element 12 to the desired focal spot F, $d_{min}$ is the distance from the array 10 to the spot F along a line perpendicular to the array 10, and $\lambda$ is the wavelength of the ultrasonic excitation signal.

Figure 2:
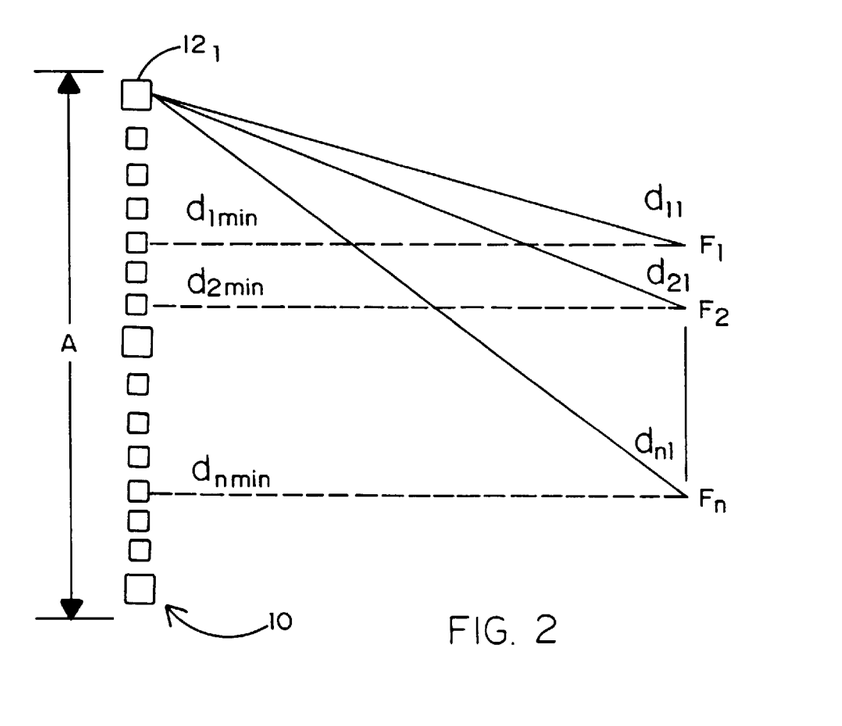
FIG. 2 is a schematic diagram illustrating the focusing of the array of FIG. 1 at a plurality of focal spots.

FIG. 2 shows the same array 10 phased to produce multiple focal spots $F_1$ and $F_2$. In order to focus the beam at $F_1$, the topmost element $12_1$ of the array 10 must be excited with a sine wave of phase $$\phi_{11} = \left(\frac{d_{11} - d_{min1}}{\lambda}\right) \times 360°, \text{ modulo } 360 \quad (2)$$

and in order to focus the beam at $F_2$, the same element must be excited with a sine wave of the same frequency but of phase $$\phi_{12} = \left(\frac{d_{12} - d_{min2}}{\lambda}\right) \times 360°, \text{ modulo } 360 \quad (3)$$

In order for the beam to focus at both $F_1$ and $F_2$, these two sine waves must be summed. It is a mathematical fact that the sum of two sine waves of the same frequency but of different phase is a sine wave of that frequency but of a resultant phase different from the phases of the component sine wave, and of a resultant amplitude different from the amplitudes of the component sine waves. In this respect, it should be understood that the amplitudes of the component sine waves may be different, so as to produce different beam intensities at different focal spots.

The foregoing calculation for two focal spots $F_1$ and $F_2$ can be expanded in the same manner to produce any number of focal spots $F_1, F_2, \ldots F_n$ which may, but need not, be aligned with each other. If the calculated phase for the $i^{th}$ element and the $j^{th}$ focal spot is $\phi_{ij}$ and the amplitude of the $j^{th}$ focal spot is $A_j$, then the resultant phase $\bar{\phi}_i$ at the $i^{th}$ element is $$\bar{\phi}_i = \tan^{-1}\left[\frac{\sum_j A_j \cos\phi_{ij}}{\sum_j A_j \sin\phi_{ij}}\right] \quad (4)$$

and the resultant amplitude $\bar{A}_i$ is $$\bar{A}_i = \left[\left(\sum_j A_j \cos\phi_{ij}\right)^2 + \left(\sum_j A_j \sin\phi_{ij}\right)^2\right]^{\frac{1}{2}} \quad (5)$$

The limitation is that the lateral separation between focal spots must be no less than the lateral resolution of the beam, which is $$\frac{\lambda d_{min\,max}}{A}$$

where $d_{min\,max}$ is the largest value of $d_{min}$ for the various focal spots, and A is the length of the array 10 in the direction transverse to the beam in FIG. 2.

Figure 3:
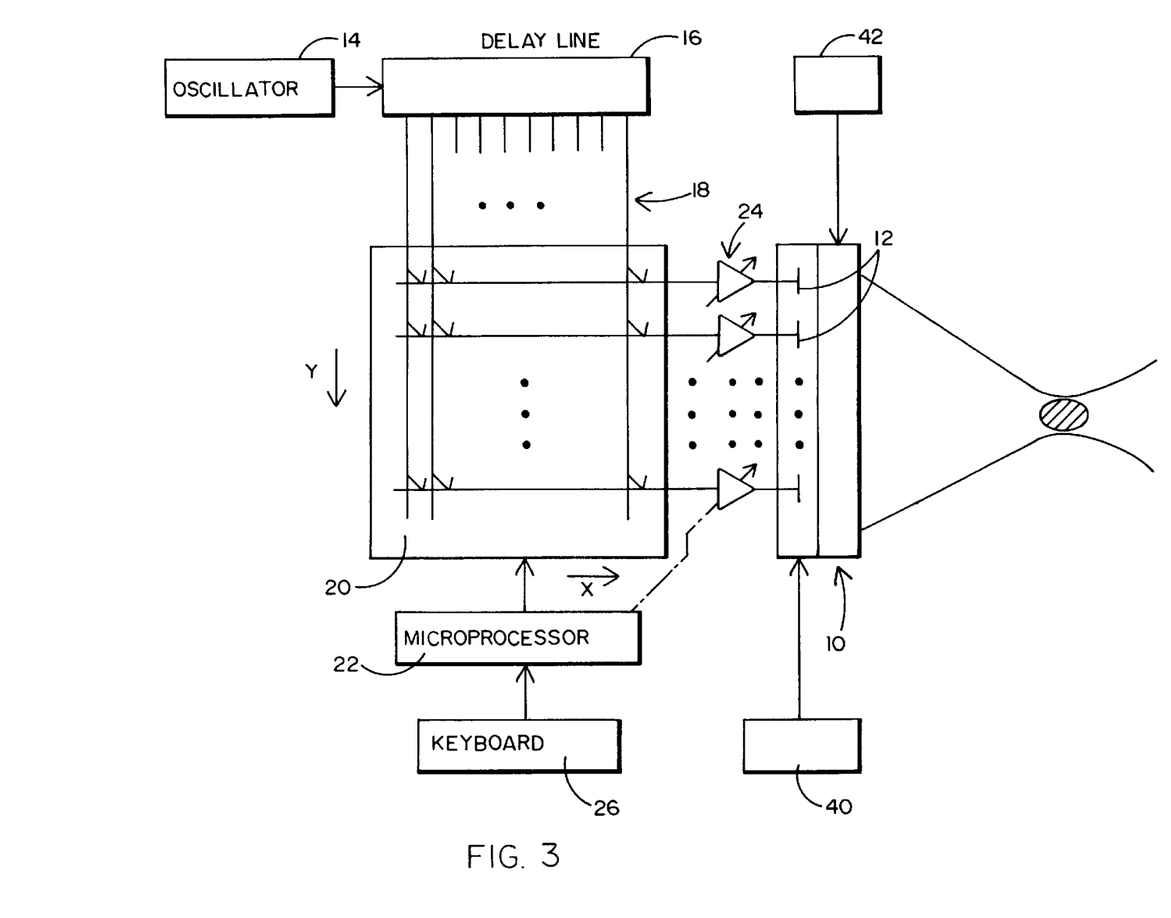
FIG. 3 is a block diagram of the inventive phasing system.

A preferred apparatus for appropriately phasing the transducer elements 12 is shown in FIG. 3. The basic ultrasonic signal produced by the oscillator 14 is applied to a tapped delay line 16. The delay line taps 18 form the y inputs of a cross point switch 20 controlled by a microprocessor 22. Each of the transducer elements 12 of the array 10 is connected to one of the x outputs of the cross point switch 20 through a variable gain amplifier 24. The gains of amplifiers 24 are also controlled by the microprocessor 22.

The delay line taps 18 are sufficiently numerous, and have small enough phase differences between them, to provide to the cross point switch 20 a sufficient selection of phases of the basic ultrasonic signal to phase the elements 12 with sufficient accuracy. In practice, this may mean, for example, 72 taps spaced by 5° of phase difference. It will be understood that each element 12 of the array 10 is connected by the cross point switch 20 to one, and only one, of the taps 18 of the delay line 16.

Figure 4:
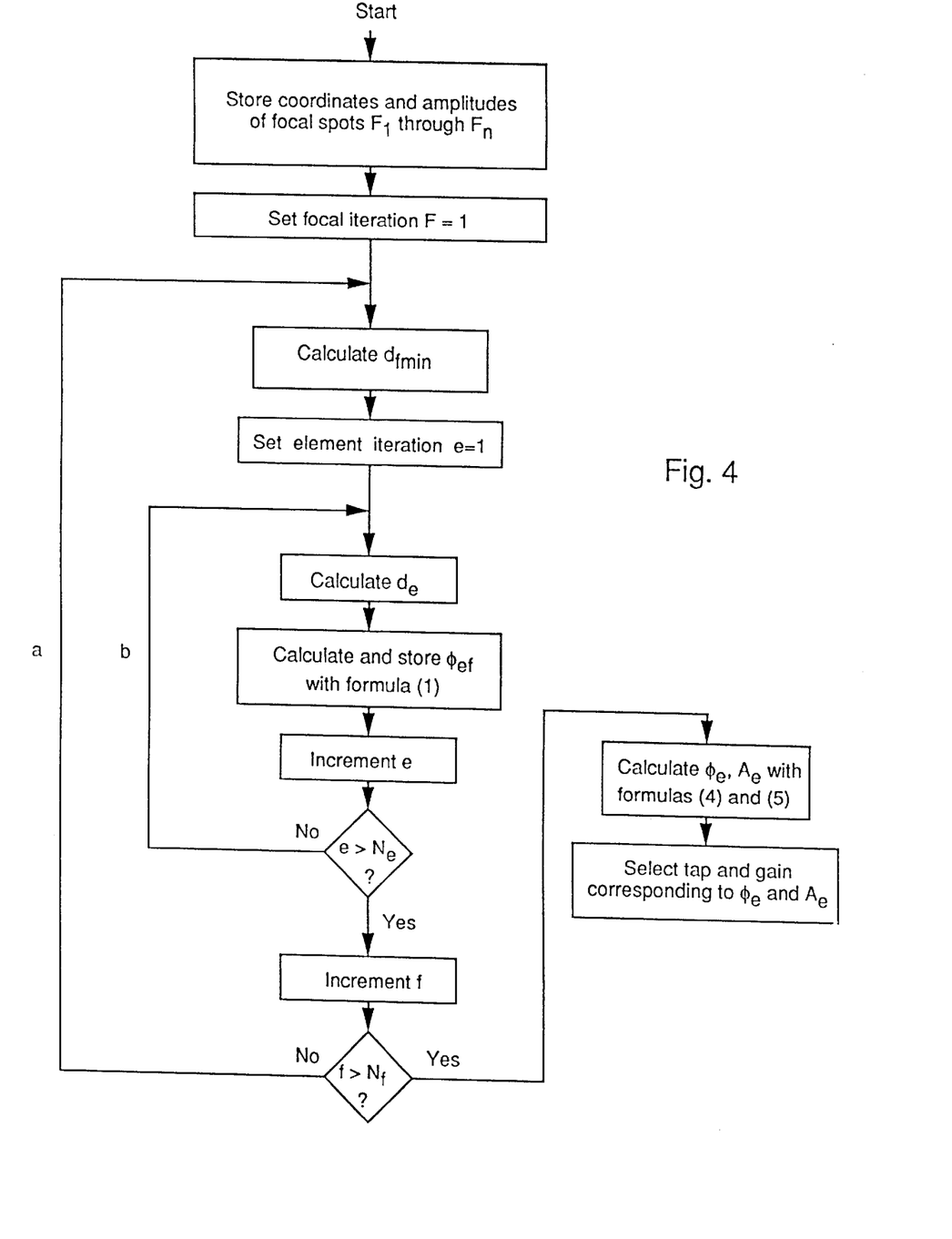
FIG. 4 is a flow chart illustrating the operation of the microprocessor of FIG. 3.

In the use of the invention, the coordinates of the desired focal spots with respect to the array 10 can be entered into the microprocessor 22 from a keyboard 26 or the like. The function of the microprocessor 22 is illustrated in the flow chart of FIG. 4. The connections in the cross point switch 20 and the relative gains of the amplifiers 24 are iteratively computed and set by the microprocessor 22. The flow chart of FIG. 4 illustrates two nested iterative routines, designated by a and b, respectively, in which routine a calculates and sets the combined phase and gain of an individual element 12 for a plurality of focal spots $F_1$ through $F_n$, while routine b repeats these calculations and settings for each of the transducer elements $12_1$ through $12_n$. In FIG. 4, f is the iteration number in routine a; e is the iteration number in routine b; $n_f$ is the number of focal spots F; $n_e$ is the number of transducer elements 12; $A_f$ is the desired beam amplitude at focal spot $F_j$; $\phi_{ef}$ is the phase needed for element $12_b$ to focus at focal spot $F_a$; $\phi_{ef}$ is the phase of the sine wave which is the sum of all the sine waves of phase $\phi_{ef}$ for an element $12_b$; and $A_e$ is the relative amplitude of the summed sine wave with respect to the amplitude of the component sine waves for element $12_b$.

Figure 5A:
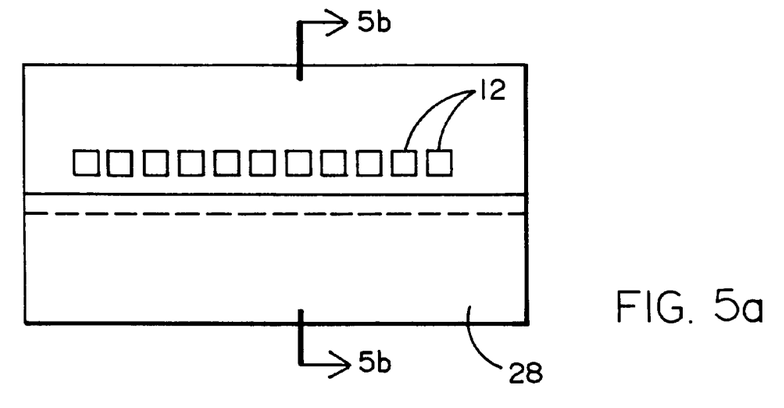
FIG. 5a is a side elevation of a line-focused array.
Figure 5B:
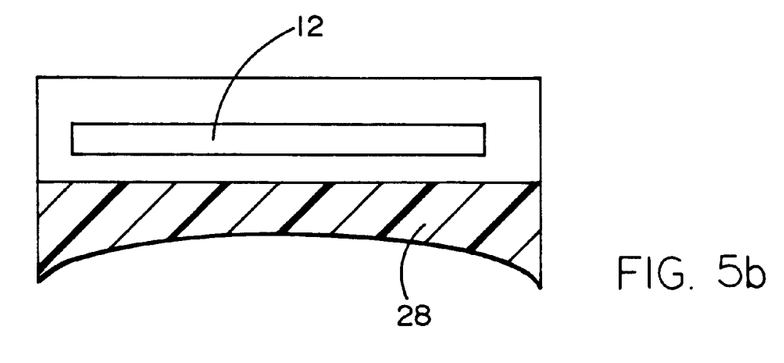
Figure 6:
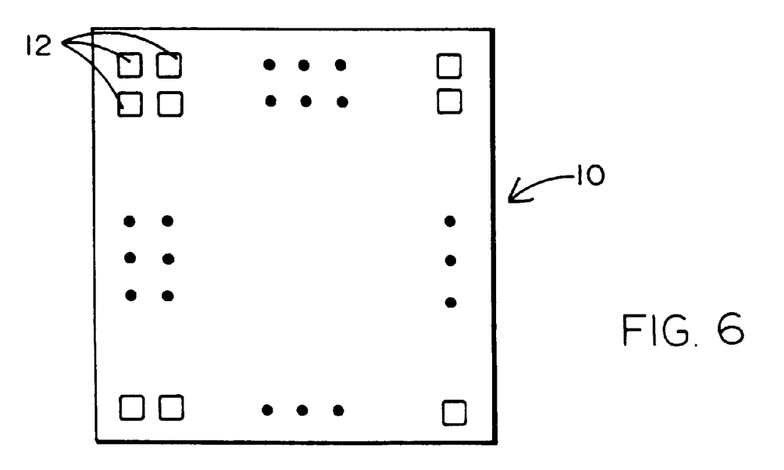
FIG. 6 is a front view of a three-dimensionally focusable array.

The foregoing discussion has assumed a one-dimensional linear array 10. As shown in FIGS. 5a and 5b, which depict a planar two-dimensional array 10 with elongated transducer elements 12, the focusing in the second dimension is typically done by a physical lens 28. As a result, the various focal spots F in such an array all lie in the same plane, which is the plane perpendicular to the lens 28 at its center. If it is desired to have the freedom of locating the focal spots F in a three-dimensional space, each elongated element 12 can be replaced with a row of individually excitable elements 12 (FIG. 6). This complicates the geometric calculation of d for each element but does not change the fact that d is the distance from the element to a selected focal spot position; consequently, the same formulae for the computation of phase remain applicable.

Figure 7:
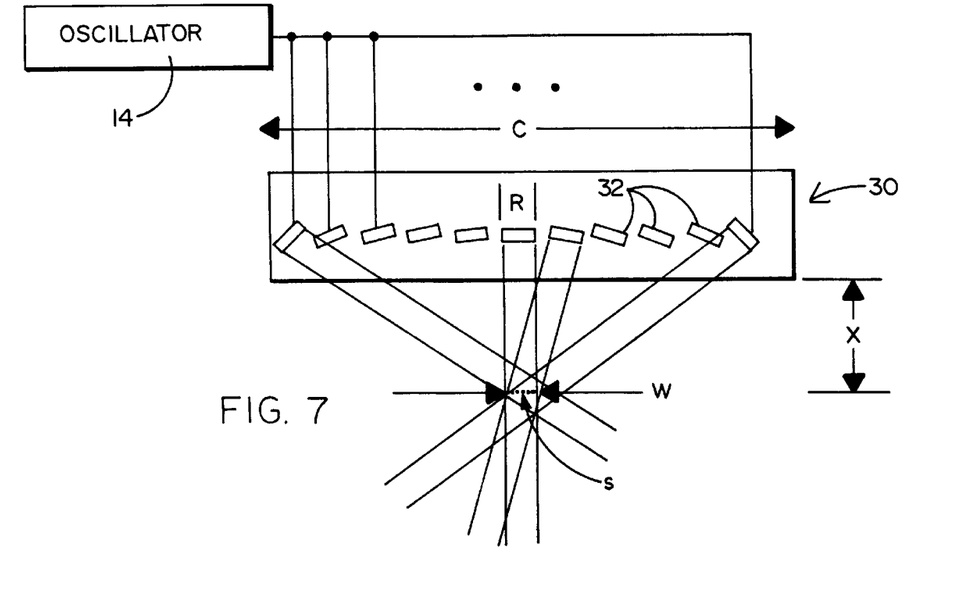
FIG. 7 is a schematic side view of an alternative embodiment of the invention.

In an alternative embodiment of the invention depicted in FIG. 7, multiple focal spots or zones can be achieved without any special drive electronics by constructing the transducer array 30 as a group of independent conventional fixed-focus transducers 32 which are focused by lenses. The array 30 would normally be aimed to produce a line of focal spots, and would thus produce a line of destroyed tissue.

The array 30 can be designed by having the transducer elements 32 widely separated. Such a transducer has grating lobes. The separation of the grating lobes is given by $$s = \lambda x / e \quad (6)$$

where $\lambda$ is the wavelength of the ultrasonic signal, x is the distance between the focal line and the plane of the array 30, and e is the lateral extent of the elements 32. The number of zones created depends on the width w of the beam created by each element. Thus, the number of focal zones created is w/s.

The advantage of this transducer over that previously described is simplicity of construction and electronic drive. The disadvantage is lack of versatility (fixed focal zones, only one line of focal zones, intensity of each focal zone fixed). However, the transducer 30 could be used with fixed focal zones in lipolytic therapy to scan these focal zones through the fat layer to create lines of dead tissue.

The apparatus of FIGS. 1–7 is extremely versatile and lends itself to a number of practical applications. As pointed out above, it allows not only the creation of any desired pattern of high-intensity focal zones in a three-dimensional space, but also allows the intensity of the ultrasound beam to be separately controlled for each of these focal zones. In addition, it is possible to dynamically change the intensities by causing the microprocessor 22 to continually recalculate the summed sine waves while changing the amplitude weightings of the component sine waves in accordance with the movement of the transducer array over a patient's body.

Figure 8:
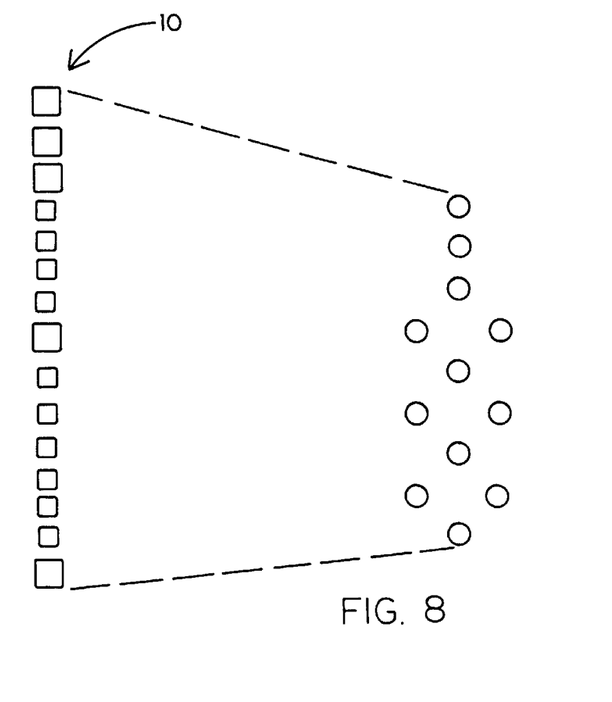
FIGS. 8–10 depict various patterns achievable with the invention.
Figure 9:
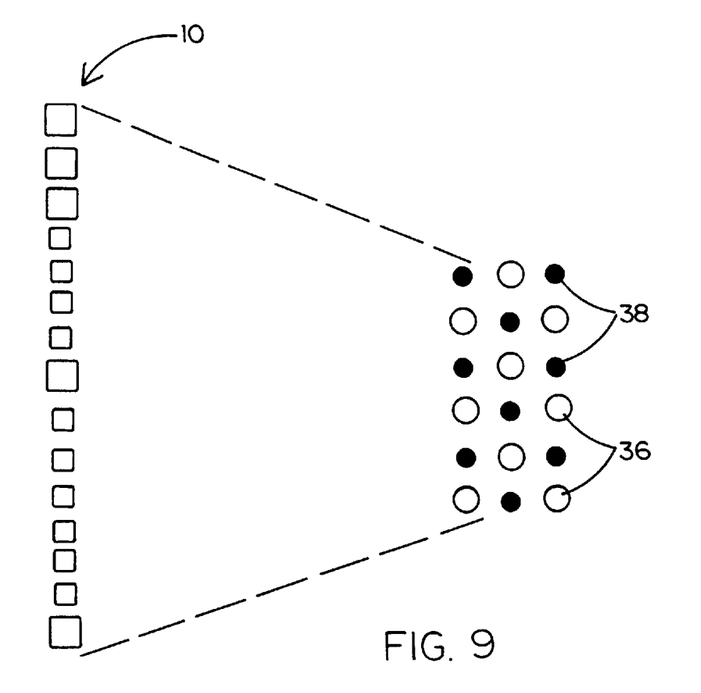
Figure 10:
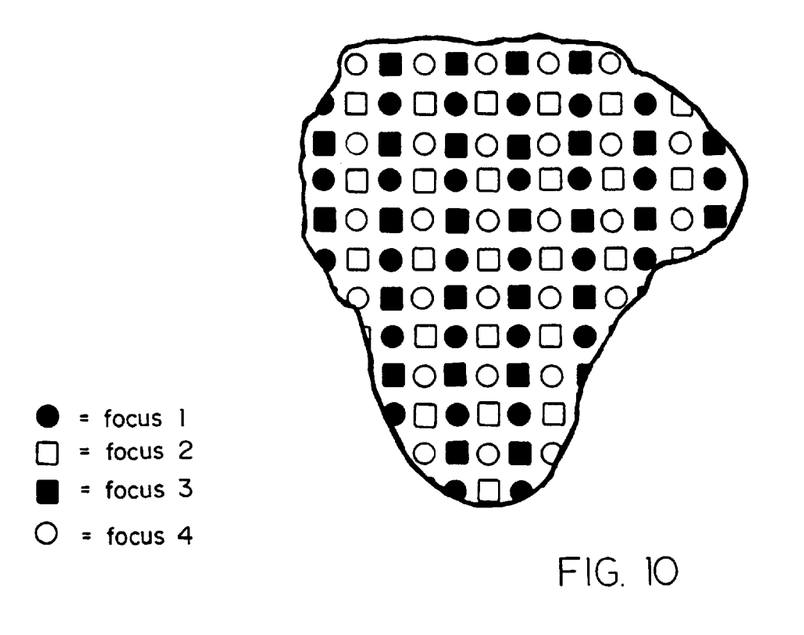

In lipolytic therapy, for example, the amplitudes may be equal in a central fat layer, then tapered near the edge (see FIG. 8). To achieve this, the microprocessor 22 may be programmed to create multiple focal layers in the central layer of fat and only one focal layer near the edge of the fat. As an alternative, the beam could be focused to groups of points, then switched between groups 36 and 38 (FIG. 9). In the extreme, the array 10 could be sequenced at high speed to each focal spot, but at power levels normally used, this would produce cavitation at each spot and could produce unpredictable results. Another alternative is to switch the position of focal zones during scanning to create isolated pockets of dead tissue. This could be done in a honeycomb-like pattern in one plane or multiple patterns in multiple planes. This last procedure allows live tissue very close to all dead tissue to provide for more rapid elimination of the dead tissue through natural body processes. It also provides for a continuous connection from one side of the fat layer to the other of live tissue. Thus, no artificial device is needed to hold the skin to underlying tissue. The array 10 can also be programmed to provide a continuous kill zone by holding the array 10 stationary and sequencing the focal patterns. FIG. 10 illustrates a sequence of four patterns. This use would be appropriate for the elimination of tumors or for the treatment of glands of arbitrary shape.

The ability of microprocessor 22 to continually recompute the phases and intensities of the transducer elements 12 make it possible to move the focal zones F in a three-dimensional space without moving or scanning the array 10. This is useful in situations where the array 10 cannot be moved, e.g. if it is used inside the patient's body.

Although the apparatus of this invention has many uses, its principal advantage is that it makes noninvasive lipolytic therapy practical. As pointed out above, in the abseneece of the invention, reducing the focal zone length to where it does not transcend the limits of the fat layer of an only slightly overweight patient results in making the focal spot so small that an inordinate and impractical length of time is required for a single focal zone to destroy a small number of fat cells.

With the multiple focal spots of this invention, however, the treatment time is greatly reduced. At the same time, the discrete focal spots produced by this invention could result in preserving a spongy structure of healthy tissue around the destroyed fat cells to support the skin and accelerate the absorption of the dead tissue.

An imaging apparatus 40 (FIG. 3) may be used to provide a quantitative diagnostic measurement of tissue depth and location prior to therapy, and to monitor the tissue destruction during the lipolytic therapy. The imaging apparatus may be of any kind well known to those skilled in the art, e.g. ultrasound imaging, CT, MRI, thermography, or the like. The ultrasound imaging apparatus may be integral with the therapy transducer and time-amplified therewith; but it may also be a separate independent device.

A fluid circulation and temperature control apparatus 42 may also be used to maintain the desired temperature of the transducer and of the skin surface which it contacts. The temperature control apparatus may be of any kind well known to those skilled in the art, e.g., electrical heat pump, evaporative cooler, large volume reservoir, or the like.

It is understood that the exemplary method and apparatus for lipolytic therapy described herein and shown in the drawings represent only a presently preferred embodiment of the invention. Indeed, various modifications and additions may be made to such embodiment without departing from the spirit and scope of the invention. Thus, other modifications and additions may be obvious to those skilled in the art and may be implemented to, adapt the present invention for use in a variety of different applications.

What is claimed is:

1. A method of selectively destroying fat cells in a subcutaneous fat layer of a living patient, comprising the steps of:

a) providing an ultrasonic transducer array arranged to produce a beam of ultrasound energy;

b) simultaneously focusing said beam in a plurality of discrete focal zones located in said fat layer; and c) applying to said focal zones an ultrasound energy level sufficient to instantaneously destroy fat cells lying in said focal zones without destroying tissue outside said focal zones;

d) said focal zones being sufficiently spaced from each other to preserve between said destroyed cells sufficient intact tissue to maintain the structural integrity of said fat layer.

2. The method of claim 1, in which the length of said focal zones in a direction perpendicular to said array is smaller than the thickness of said fat layer.

3. The method of claim 1, in which said transducer array is located outside the body of said patient, and said ultrasound energy beam is transmitted transcutaneously.

4. The method of claim 1, further comprising the step of using said array to also image said subcutaneous fat layer.

5. The method of claim 1, further comprising the step of diagnostically imaging said subcutaneous fat layer prior to said ultrasound energy application.

6. The method of claim 1, further comprising the step of imaging said subcutaneous fat layer during and subsequent to said ultrasound energy application to monitor the ablation of said fat layer.

7. The method of claim 1, further comprising the step of maintaining said array and said patient's skin surface at a predetermined temperature during application of said ultrasonic energy.

* * * * *